(12) United States Patent
Seo et al.

(10) Patent No.: US 12,139,715 B2
(45) Date of Patent: Nov. 12, 2024

(54) GENE EXPRESSION CASSETTE CAPABLE OF INITIATING TRANSLATION AFTER COMPLETION OF TRANSCRIPTION FOR PRODUCING HIGH-QUALITY RECOMBINANT PROTEIN IN BACTERIA

(71) Applicant: SEOUL NATIONAL UNIVERSITY R&DB FOUNDATION, Seoul (KR)

(72) Inventors: Sang Woo Seo, Seoul (KR); Jina Yang, Seoul (KR)

(73) Assignee: SEOUL NATIONAL UNIVERSITY R&DB FOUNDATION, Seoul (KR)

(*) Notice: Subject to any disclaimer, the term of this patent is extended or adjusted under 35 U.S.C. 154(b) by 1000 days.

(21) Appl. No.: 17/253,401

(22) PCT Filed: Jun. 19, 2018

(86) PCT No.: PCT/KR2018/006924
§ 371 (c)(1),
(2) Date: Dec. 17, 2020

(87) PCT Pub. No.: WO2019/245066
PCT Pub. Date: Dec. 26, 2019

(65) Prior Publication Data
US 2021/0340551 A1    Nov. 4, 2021

(30) Foreign Application Priority Data

Jun. 19, 2018  (KR) .......................... 10-2018-0070484

(51) Int. Cl.
*C12N 15/67*          (2006.01)
(52) U.S. Cl.
CPC .......... *C12N 15/67* (2013.01); *C12N 2840/55* (2013.01)
(58) Field of Classification Search
CPC ..... C12N 15/67; C12N 2840/55; C12N 15/70
See application file for complete search history.

(56) References Cited

U.S. PATENT DOCUMENTS

2017/0204477 A1*  7/2017  Green ................. C12Q 1/6897

FOREIGN PATENT DOCUMENTS

| JP | 2012-183068 A | 9/2012 |
|---|---|---|
| KR | 0127560 B1 | 12/1997 |
| KR | 10-2000-0057704 A | 9/2000 |
| KR | 10-0454533 B1 | 11/2004 |
| KR | 10-1032871 B1 | 5/2011 |
| KR | 10-1349070 B1 | 1/2014 |
| KR | 10-1350355 B1 | 1/2014 |
| KR | 10-2015-0083115 A | 7/2015 |
| KR | 10-2017-0132874 A | 12/2017 |
| WO | 2017/040829 A1 | 3/2017 |
| WO | 2017/147585 A1 | 8/2017 |
| WO | 2018/026765 A1 | 2/2018 |

OTHER PUBLICATIONS

Qu (Cancer letters 365.2 (2015): 141-148) (Year: 2015).*
Igor Ruiz De Los Mozos et al., "Base Pairing Interaction between 5'- and 3'-UTRs Controls icaR mRNA Translation in *Staphylococcus aureus*", PLOS Genetics, Dec. 2013, p. 1-18, vol. 9, Issue 12.
Naomi Balaban et al., "Translation of RNAIII, the *Staphylococcus aureus* agr regulatory RNA molecule, can be activated by a 3'-end deletion", FEMS Microbiology Letters 133, 1995, pp. 155-161.
Thomas Thisted et al., "Mechanism of Post-segregational Killing: Secondary Structure Analysis of the Entire Hok mRNA from Plasmid R1 Suggests a Fold-back Structure that Prevents Translation and Antisense RNA Binding", Journal of Moleclar Biology, 1995, pp. 859-873, vol. 247.
James Chappell et al., "A renaissance in RNA synthetic biology: new mechanisms, applications and tools for the future", Current Opinion in Chemical Biology, 2015, pp. 47-56, vol. 28.
Sven Findeiß et al., "Design of Artificial Riboswitches as Biosensors", Sensors, 2017, 28pages, vol. 17, No. 1990.
Andreas Wachter, "Riboswitch-mediated control of gene expression in eukaryotes", RNA Biology, 2010, p. 67-76, vol. 7, No. 1.
Magali Naville et al., "Transcription attenuation in bacteria: theme and variations", Briefing in Functional Genomics and Proteomics, p. 482-492, vol. 8, No. 6.
International Search Report for PCT/KR2018/006924 dated May 15, 2019 [PCT/ISA/210].

* cited by examiner

*Primary Examiner* — Nancy J Leith
*Assistant Examiner* — Kyle T Rega
(74) *Attorney, Agent, or Firm* — Sughrue Mion, PLLC

(57) ABSTRACT

Provided is a gene expression cassette which, for the production of a high-quality recombinant protein in bacteria, initiates translation after completion of transcription, and more specifically, to a gene expression cassette consisting of a switch capable of stopping translation initiation and a trigger system capable of activating the translation initiation from the switch by re-configuring the transcription-translation coupled system inherent in bacteria such that the translation is initiated only by a full-length mRNA chain template. The transcription and translation in the bacteria can be uncoupled by inserting a trigger sequence activating the translation initiation from the switch into the downstream (3' terminal) of a target recombinant gene by replacing a natural transcription translation-coupled 5' UTR with the switch. The productivity of a high-quality full-length recombinant protein can be increased while reducing the costs associated with a purification process.

6 Claims, 8 Drawing Sheets
Specification includes a Sequence Listing.

GENE EXPRESSION CASSETTE CAPABLE OF INITIATING TRANSLATION AFTER COMPLETION OF TRANSCRIPTION FOR PRODUCING HIGH-QUALITY RECOMBINANT PROTEIN IN BACTERIA

CROSS REFERENCE TO RELATED APPLICATIONS

This application is a National Stage Application No. PCT/KR2018/006924, filed on Jun. 19, 2018, which claims priority from Korean Patent Application No. KR 10-2018-0070484 filed Jun. 19, 2018, the entire disclosures of which are incorporated herein by reference.

INCORPORATION BY REFERENCE OF SEQUENCE LISTING

The content of the electronically submitted sequence listing, file name: Q260028 substitute sequence listing; size: 15,207 bytes; and date of creation: Jun. 24, 2021, filed Jul. 19, 2021, is incorporated herein by reference in its entirety.

TECHNICAL FIELD

The present invention relates to a gene expression cassette for increasing the productivity of a full-length recombinant protein in a process of culturing a microorganism to produce a recombinant protein, and more particularly to a gene expression cassette that uses a switch and a trigger to perform control such that translation is initiated using only full-length mRNA having an intact end as a template by reconstructing the transcription and translation systems present in an organism.

BACKGROUND ART

In bacteria, when the translation initiation sequence is naturally exposed during the transcription stage, the translation initiation stage proceeds at the same time. This phenomenon is called "transcription-translation coupling" or "co-transcriptional translation". In bacteria, about 4% of intracellular mRNA exists without a stop codon due to early termination of transcription and cleavage of mRNA. When co-transcriptional translation occurs, translation is initiated from prematurely transcription-terminated mRNA without completion of transcription. Translation from prematurely transcription-terminated mRNA as a template may cause problems including production of polypeptides having no function and waste of cellular resources such as amino acids and ATP.

Although bacteria have ribosome recovery systems such as tmRNA, which mediates trans-translation, and ArfA-Release factor 2, which induces ribosome-releasing factors, it is difficult to solve these problems using only the systems inherent in cells. In addition, when the recombinant protein is overexpressed, prematurely terminated mRNAs accumulate, making it difficult to resolve mRNA having no stop codon.

Meanwhile, in order to produce recombinant proteins for polymers and most highly functional products, both productivity and the quality of the final product are important. Conventional studies for this purpose include removing proteolytic enzymes from production strains, improving cell lines to self-supply amino acids contained in greater amounts in the target proteins, increasing the number of copies of genes, and improving transcription and translation efficiency by promoter engineering and redesigning 5' UTR.

In addition, in recent years, techniques to reconstruct genes with codons optimized for hosts and studies to homogenize the codon frequency pattern with the sources of genes have been attempted along with the ribosome-profiling technique, and signal peptides for expressing functionalities of recombinant proteins are being developed using a method of refolding a large amount of expressed protein into a functional construct after purification and a high-throughput screening method.

Signal peptides for expression of functionalities are being developed.

However, techniques developed to date are mainly used for the purpose of increasing the yield of poorly expressed proteins, expressing these proteins as functional constructs and purifying the expressed proteins. In order to maintain the efficacy of the recombinant protein, which is a polymer, a process for removing impurities in the purification process is required, and there is a problem in that the cost of the purification process is burdensome.

Therefore, there is need for development of a system capable of producing high-productivity and high-quality recombinant proteins while reducing the burden of the cost required for the purification process without damage.

DISCLOSURE

Technical Problem

Therefore, the present invention has been made to solve the above problems, and it is one object of the present invention to provide a gene expression cassette having a system including a switch that performs control such that translation initiation is conducted only from a full-length mRNA template and a trigger that can activate translation initiation from the switch by reconstructing the transcription-translation coupling system inherent in bacteria. In addition, it is another object to provide technology that increases the productivity of a full-length high-quality recombinant protein while reducing the burden of the cost of the purification process.

Technical Solution

In accordance with a first aspect of the present invention, the above and other objects can be accomplished by the provision of a DNA molecule capable of forming a stem loop structure during transcription into mRNA, the stem loop structure having a ribosome-binding site located therein, the DNA molecule including a DNA sequence (a) encoding an RNA sequence designed for a part of the sequence to participate in the formation of the stem loop structure, and a DNA sequence (b) encoding an RNA sequence complementarily binding to the RNA sequence designed for the part of the sequence to participate in the formation of the stem loop structure, and being located after a stop codon.

In the first aspect of the present invention, the DNA molecule preferably includes a multiple cloning site after the ribosome-binding site and before the DNA sequence (b).

In accordance with a second aspect of the present invention, provided is a vector including the DNA molecule according to the first aspect.

In accordance with a third aspect of the present invention, provided is an mRNA forming a stem loop structure, the stem loop structure having a ribosome-binding site located therein, the mRNA including an RNA sequence (a) having a part of the sequence participating in the stem loop structure, and an RNA sequence (b) having a complementary sequence capable of binding to the RNA sequence (a) and being located after a stop codon.

In the third aspect of the present invention, the mRNA preferably initiates translation while the stem loop structure is released when the RNA sequence (b) binds to the RNA sequence (a). In this case, the translation is preferably initiated when the ribosome binds to the ribosome-binding site.

Advantageous Effects

According to the present invention, an uncoupling system of transcription and translation stages is realized by introducing a so-called switch sequence and a trigger sequence into the mRNA. As a result, translation is initiated only when conducting transcription to the target 3' end, so full-length high-quality recombinant proteins can be produced.

Meanwhile, the recombinant protein produced according to the present invention can be used in a variety of industries from pharmaceuticals and antibodies to raw materials for functional cosmetics, detergents, fertilizers, and feed for livestock.

BRIEF DESCRIPTION OF DRAWINGS a) of FIG. 1 is a schematic diagram illustrating the mechanism of operation of a ProQC gene expression cassette in which a trigger sequence for initiating translation from a switch is located in the same mRNA as the switch, and b) of FIG. 1 is a schematic diagram illustrating whether or not a ribosome binds to a ribosome-binding site (RBS) in the respective cases of mRNA having switch and trigger sequences and mRNA not having switch and trigger sequences.

Figure 7:
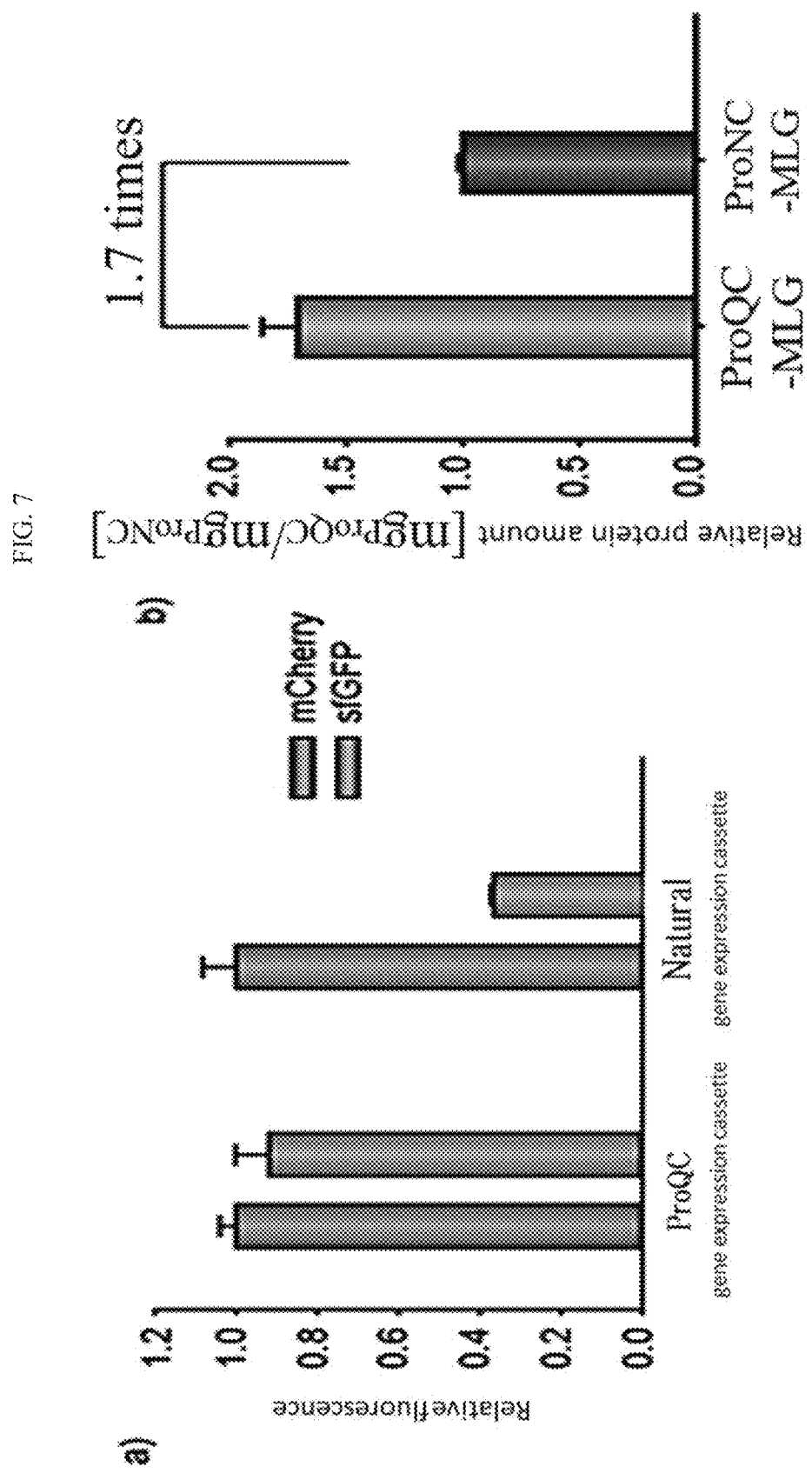

a) of FIG. 7 is a graph showing the amounts of amino and carboxyl ends of the MLG fusion protein of each of ProQC-MLG and ProNC-MLG strains, wherein fluorescence per cell is calculated by dividing mCherry and sfGFP fluorescence by the absorbance at a wavelength of 600 nm, and the fluorescence per cell is converted to the amount of each fluorescent protein and then normalized to the amount of mCherry, and b) of FIG. 7 is a graph comparing the expression level of full-length protein (based on the sfGFP at the carboxyl end), when the unit fluorescence of ProNC-sfGFP is normalized to 1, in order to determine the productivity of the fusion protein of unit cells in ProQC-MLG and ProNC-MLG.

Figure 8:
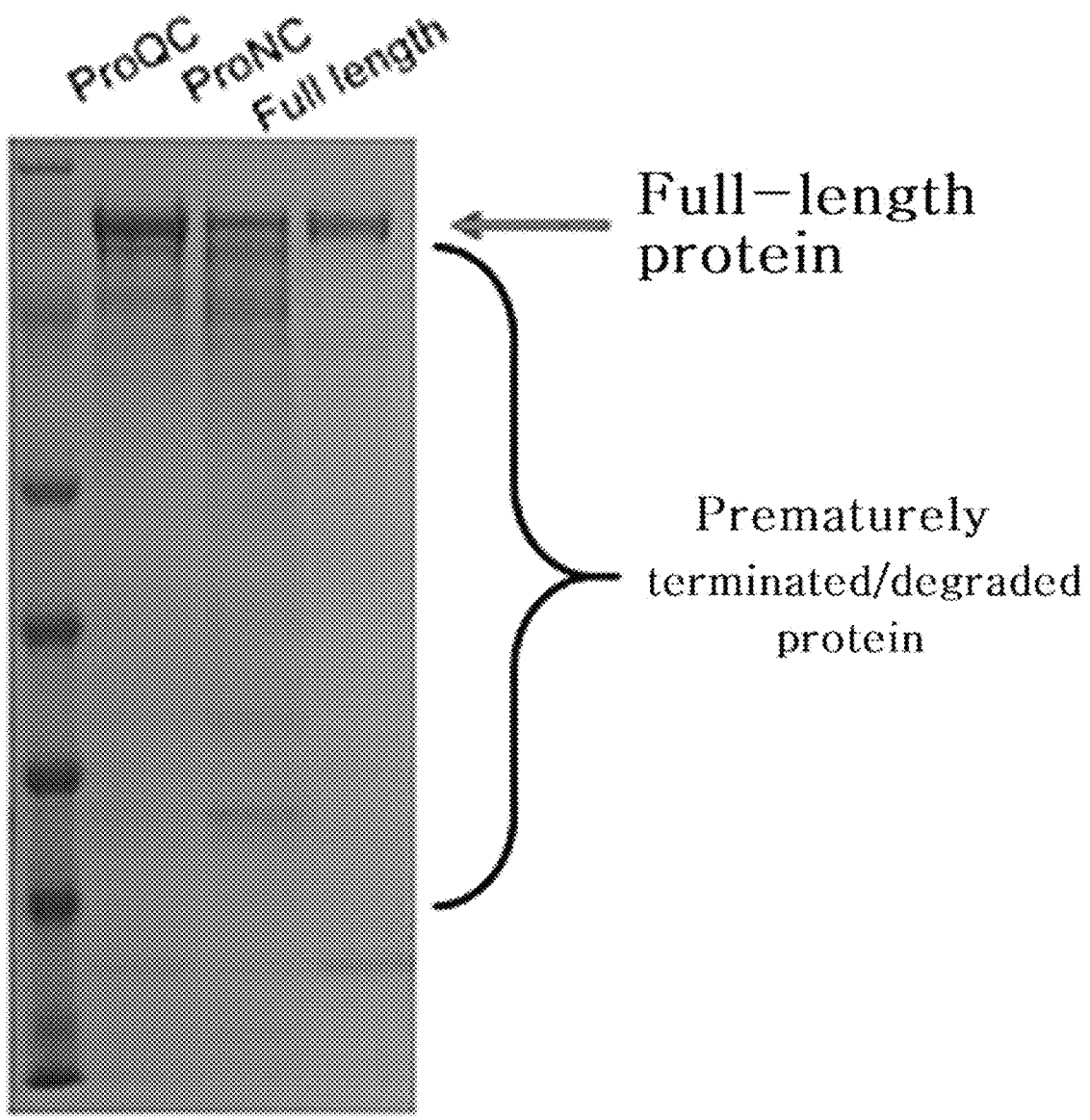

FIG. 8 shows the result of SDS-PAGE of proteins expressed from the ProQC-MLG strain and the ProNC-MLG (control) strain, wherein Full length represents a fusion protein purified using a histidine tag at the carboxy terminal as a full-length marker.

BEST MODE

The present invention provides a gene expression cassette that is capable of releasing the transcription-translational coupling of bacteria and allowing translation to be initiated only in the mRNA strand in which transcription has been completed. That is, the present invention provides a gene expression cassette that includes a nucleic acid sequence preventing the initiation of translation of an mRNA template transcribed to an incomplete length (hereinafter referred to as a "switch") and a nucleic acid sequence capable of binding to the switch upon transcription of the full length thereof to activate translation initiation (hereinafter referred to as a "trigger"). More specifically, after complete termination of transcription, when the trigger nucleic acid sequence at the 3' end of the mRNA is exposed to the mRNA and binds complementarily to the switch sequence at the 5' UTR of the mRNA, the stem loop structure in which the switch sequence particulates is released, thus resulting in translation initiation. The transcriptional translation non-coupling system of the present invention enables a full-length, high-quality recombinant protein to be produced in bacteria.

Figure 1:
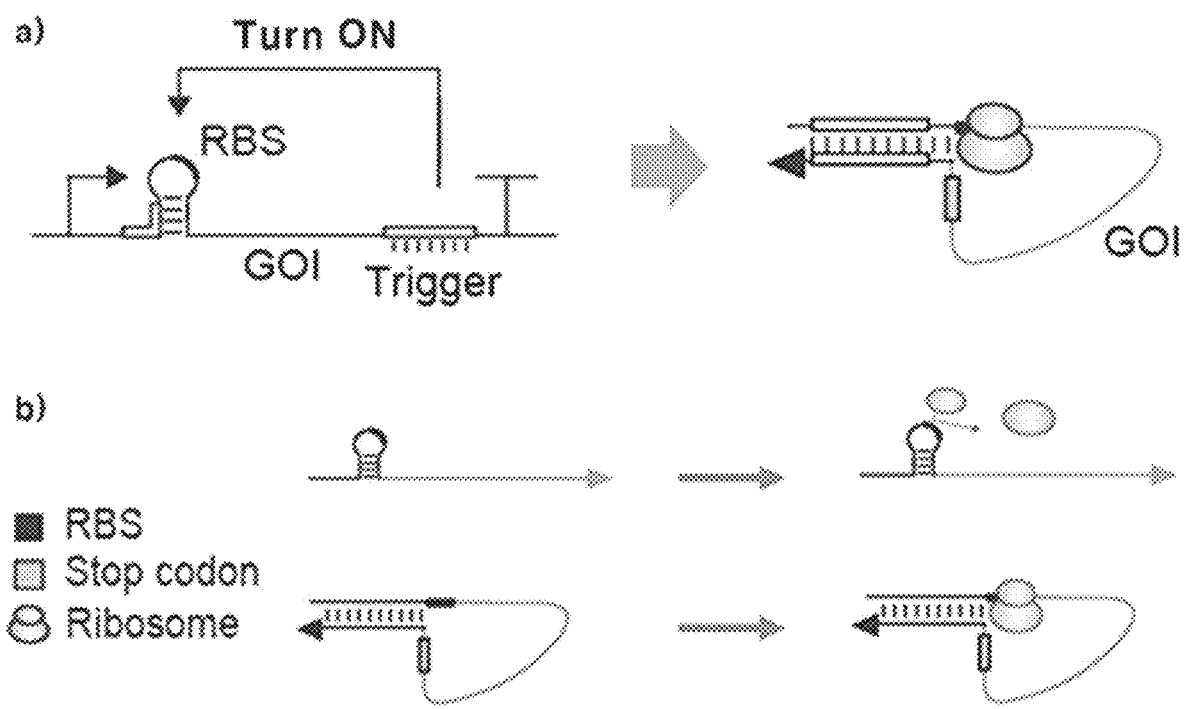

A schematic diagram of the gene expression cassette of the present invention is illustrated in FIG. 1. The mRNA molecule transcribed from DNA in bacteria has a sequence capable of binding to a ribosome, that is, a ribosome-binding site (RBS) thereon. When the ribosome binds to this ribosome-binding site, translation can be initiated. Additionally, the present invention aims to control the time point at which translation is initiated through the so-called "switch-trigger system" of the present invention.

The schematic diagram of FIG. 1 will be described in detail. The so-called switch sequence (RNA sequence (a) in the present invention) and the trigger sequence (RNA sequence (b) in the present invention) of the present invention are present in the same mRNA strand. A part of the switch sequence participates in the formation of the stem loop structure containing RBS. The trigger sequence (RNA sequence (b) in the present invention) is located at the 3' end of the same mRNA, preferably after the stop codon.

When the stem loop structure is formed, translation is not initiated. In the case of a fully transcribed mRNA, the trigger sequence is exposed onto the mRNA, and the exposed mRNA binds to the complementary switch sequence to release the stem loop structure and thereby induce initiation of translation. That is, the trigger sequence that initiates translation from the switch is located in the same mRNA as the switch. As shown in a) of FIG. 1, when the trigger sequence at the 3' end of the mRNA is exposed onto the mRNA through a complete transcription process, it pairs with the switch sequence of 5' UTR and binds complementarily thereto to form a signal for initiating (turning on)

translation. When the ribosome binds to the ribosome-binding site in the state in which the switch and trigger sequences complementary bind to each other, translation is initiated normally, and when the translation is terminated by a stop codon located in front of the trigger sequence, a complete protein can be produced from a complete mRNA template having an intact 3' end.

When the gene expression cassette of the present invention is used, as shown in b) of FIG. 1, it can be seen that translation cannot be initiated because the ribosome cannot bind to the ribosome-binding site of an mRNA having no switch-trigger system, whereas translation can be initiated because the ribosome binds only to the mRNA ribosome-binding site having the switch-trigger system according to the present invention.

Meanwhile, in the present invention, a part of the switch sequence preferably participates in the formation of the stem loop structure. When the entirety of the switch sequence participates in the formation of the stem loop structure, even if the trigger sequence complementarily binds to the switch sequence, the binding force of the trigger sequence participating in the stem loop structure formation is equal to the binding force with the trigger sequence, making it difficult to release the formation of the stem loop structure.

Meanwhile, in a second aspect, the present invention provides a DNA molecule capable of forming a stem loop structure during transcription into mRNA, the stem loop structure having a ribosome-binding site located therein, the DNA molecule including a DNA sequence (a) encoding an RNA sequence designed for a part of the sequence to participate in the formation of the stem loop structure, and a DNA sequence (b) encoding an RNA sequence complementarily binding to the RNA sequence designed for a part of the sequence to participate in the formation of the stem loop structure, and being located after a stop codon, and a vector including the DNA molecule.

In the second aspect of the present invention, a switch-trigger system operated at the mRNA level is implemented on DNA, and the DNA of the present invention functions as a gene expression cassette system that ensures high-efficiency expression of the target protein, and the vector including the DNA molecule according to the second aspect of the present invention functions to transport this expression system. The bacterium transformed with the vector of the present invention can produce a target protein in an intact form, as described above, and thus can produce a recombinant target protein with high efficiency.

Meanwhile, in the present invention, a variety of promoters and terminators required for initiation and termination of expression can be designed, and the amount of the target protein can be adjusted according to the intensity of the promoter.

Meanwhile, in the present invention, the DNA molecule preferably includes a multiple cloning site after the ribosome-binding site and before the DNA sequence (b) (the so-called "trigger" sequence), and various genes encoding target proteins can be inserted into the multiple cloning site.

Hereinafter, the present invention will be described in more detail with reference to the following examples, but the scope of the present invention is not limited to the examples, and includes variations and technical concepts equivalent thereto.

Example 1: Production of Transcriptional-Translation Uncoupling Gene Expression Cassette In order to construct a synthetic gene expression cassette (ProQC gene expression cassette) that allows translation to be initiated only in the mRNA strand that has been completely transcribed in bacteria, a T7 promoter, which is a strong promoter widely used in the production of recombinant proteins, was used. Mach-TIR strains were used for all cloning in the example.

First, the vector section containing the chloramphenicol resistance gene (CamR) was amplified using the ECONI-PT7-NheI-TT7-F/SpeI-pACYC-R primer set shown in Table 2 and a pACYC_Duet plasmid as a template to remove unnecessary restriction enzyme sites from the vector. By cloning the pACYC_Duet plasmid using EcoNI and NheI and the amplified PCR product using EcoNI and SpeI restriction enzymes, respectively, the NheI restriction enzyme sequence of the existing plasmid was removed, and pACYC* in which a cloning site capable of accommodating a gene expression cassette is inserted between the T7 promoter and T7 terminator sequences was constructed.

Figure 2:
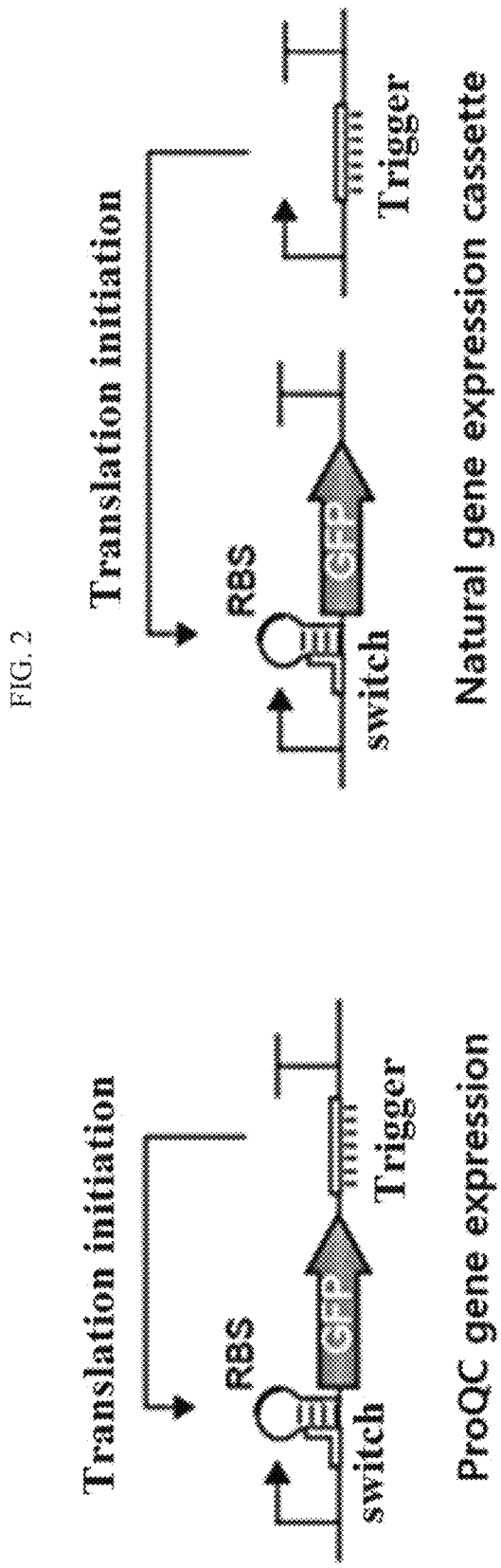
FIG. 2 is a schematic diagram illustrating a txtl-Cis-sfGFP gene expression cassette in which a trigger sequence for initiating translation from a switch is located in the same mRNA as the switch, and is a schematic diagram illustrating a natural gene expression cassette (txtl-Trans-sfGFP) in which a trigger is located in a plasmid different from the switch expressing the target gene.

The conventional switch and trigger systems for controlling the initiation of translation facilitate translation initiation in the presence of a trigger by transcribing the trigger sequence from plasmids having a high number of copies or relatively strong promoters. However, in the present invention, one trigger molecule is present per switch for initiating translation, that is, at an equal ratio. For this reason, in order to determine whether or not translation initiation occurs smoothly even under conditions where there are not many trigger molecules, a genetic circuit was constructed using green fluorescent protein (sfGFP) as a reporter, as shown in FIG. 2.

Next, sfGFP was primarily amplified using a pBR322-J23100-sfGFP plasmid as a template and a Swit-sfGFP-F1/SpeI-SacI-sfGFP-R primer set shown in Table 2, and was then amplified again using a BsaI-Swit-sfGFP-F2/BsaI-Trig-R2 primer set, a toehold switch was attached to the 5' end of the sfGFP, and a trigger sequence was attached to the 3' end thereof. After cutting the pACYC* vector with BsaI and NheI restriction enzymes, the amplification product was cloned using the BsaI restriction enzyme sequence to construct a txtl-Cis-sfGFP plasmid, and the amplification product was cloned using the BsaI and SpeI restriction enzyme sequences to construct a txtl-Trans-sfGFP plasmid. Further, plasmids for transcribing the trigger for gene expression of the txtl-Trans-sfGFP plasmid were constructed.

The sequence from the T7 promoter to the T7 terminator of pACYC* was cloned into a pCDF Duet vector using EcoNI and Bsu36I restriction enzyme sequences to construct a pCDF-Term plasmid, and a trigger sequence amplified using a BsaI-Trigger #3-F/BsaI-Trig-R2 primer set shown in Table 2 was cut with a BsaI restriction enzyme, and was then cloned into a pCDF-Term vector cut with BsaI and NheI restriction enzymes to construct a pCDF-Trigger plasmid.

Since the pCDF-Trigger plasmid has a higher number of copies (about 40 copies per cell) than the pACYC_Duet plasmid (about 12 to 15 copies per cell), and is continuously supplied, translation from the natural gene expression cassette is initiated independently of transcription termination of sfGFP.

Experimental Example 1: Determination of ProQC Gene Expression Cassette Efficiency In order to compare the translation initiation efficiency from the constructed ProQC gene expression cassette with that of the natural gene expression cassette, a pair of a txtl-Cis-sfGFP plasmid and a pCDF-Term plasmid, and a pair of a Trans-sfGFP plasmid and a pCDF-Trigger plasmid were transformed into *Escherichia coli* BL21 (DE3), which is widely used for recombinant protein production.

Screening was conducted on a plate containing spectinomycin (Spec, 50 ug/mL) and chloramphenicol (Cam, 34 ug/mL) antibiotics to maintain the plasmid, the formed colonies were inoculated into a liquid LB (Lysogeny broth) medium supplemented with Spec and Cam and grown overnight, and the absorbance was measured using a UV-1700 spectrophotometer.

After dilution to the initial absorbance ($OD_{600}$; optical density at 600 nm) of 0.05, incubation was conducted until $OD_{600}$ reached 0.8, followed by induction with 0.2 mM IPTG. At 4 hours, a certain volume of cells was harvested and washed with a PBS (phosphate-buffered saline) buffer, and fluorescence was measured using a Hydex filter for wavelengths of 486 nm and 535 nm. The experiment for measuring fluorescence was performed in triplicate, and the value, measured with a multiplate reader, was divided by the $OD_{600}$ of each sample to convert the same to fluorescence per cell.

Figure 3:
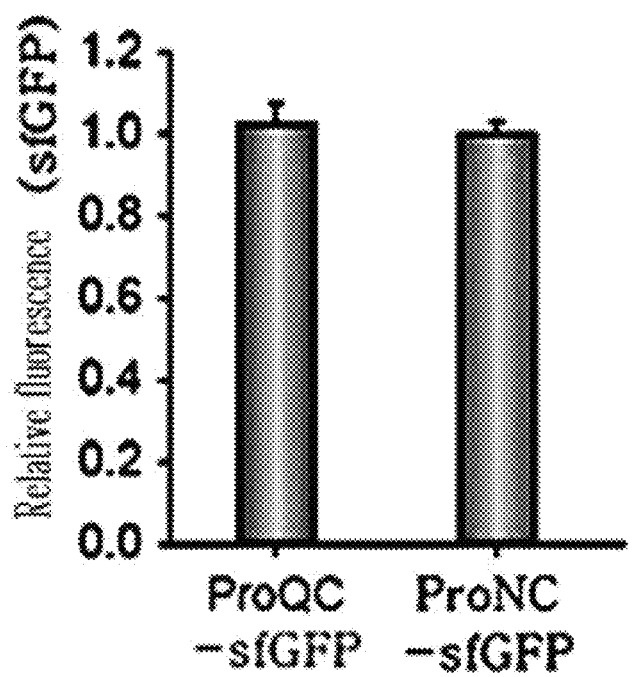
FIG. 3 is a graph comparing unit fluorescence obtained by expressing the reporter protein sfGFP in the ProQC gene expression cassette and the natural gene expression cassette, and normalizing the unit fluorescence in each system with the expression value of the natural gene expression cassette (unit fluorescence of ProNC-sfGFP=1).

As a result, as can be seen from FIG. 3, based on the relative fluorescence when the fluorescence in the natural gene expression system is set to 1, the translation initiation efficiency of the ProQC gene expression cassette (ProQC-sfGFP) is almost the same as that of the natural gene expression system (ProNC-sfGFP).

Experimental Example 2: Construction of Genetic Circuit for Measuring Intramolecular and Intermolecular Interactions of Switch and Trigger Sequences of mRNA, and Measurement of mRNA Intramolecular and Intermolecular Interactions There are a variety of molecules in cells. In particular, when a lot of mRNA is transcribed from a T7 promoter, which has a strong intensity, translation can also be initiated from the switch of the mRNA strand having no trigger through intermolecular interaction by a trigger at the 3' end of another mRNA.

In order to create a system that allows translation to be initiated from an intact full-length mRNA by controlling the translation to be initiated by a trigger at the 3' end, which is exposed upon termination of transcription, the interaction within one mRNA molecule should be stronger than the interaction between mRNA molecules.

Thus, in order to verify this, by introducing different reporter proteins into one switch and removing a trigger from the mRNA of one reporter protein, a gene circuit that does not initiate translation only using the corresponding mRNA was designed and constructed.

Figure 4:
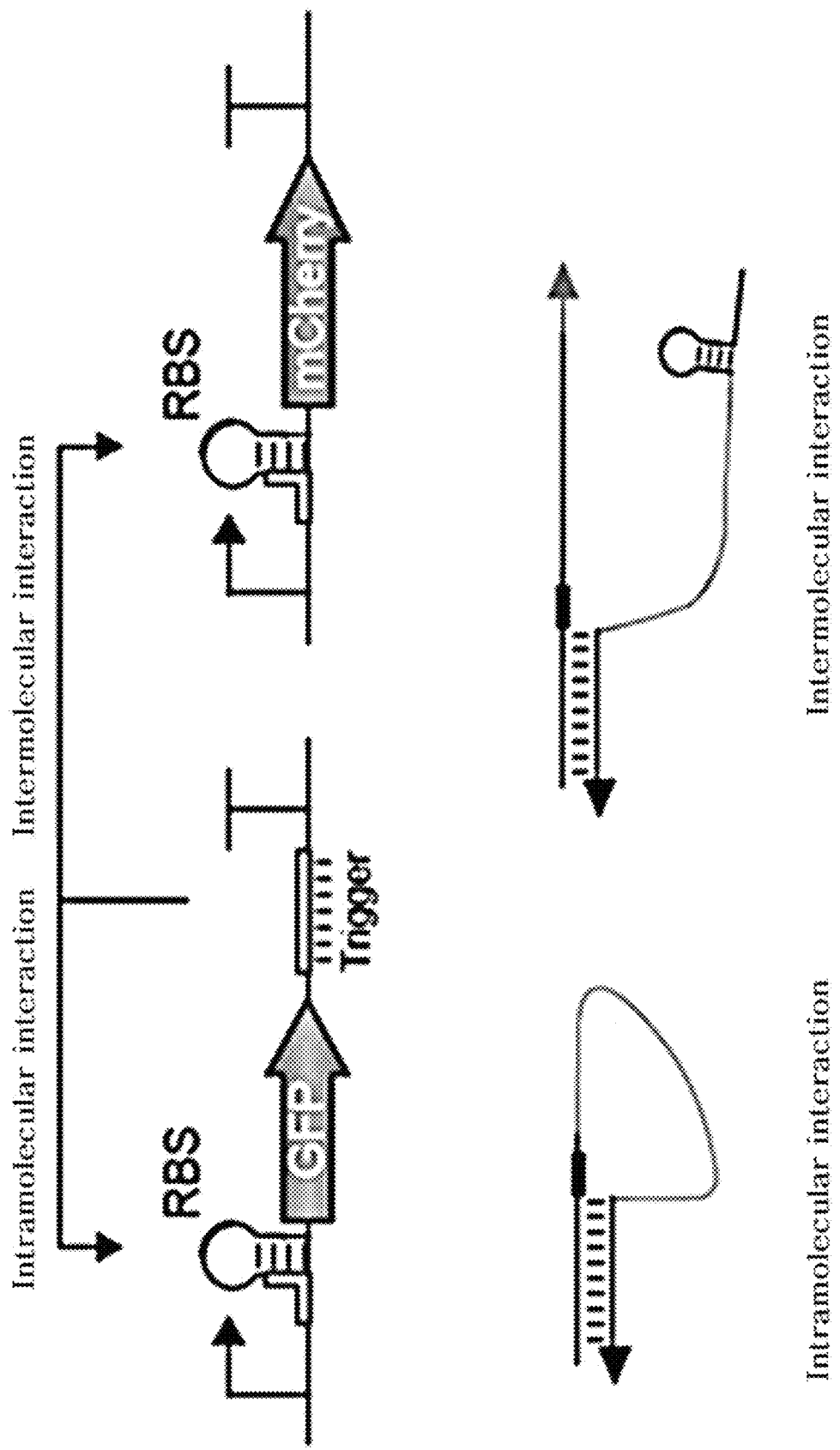
FIG. 4 is a genetic circuit diagram showing the degree of intramolecular and intermolecular interactions of the switch and trigger sequences of mRNA transcribed in the ProQC gene expression cassette.

Since the conventional mCherry sequence has an unintended translation initiation sequence at the amino terminal, the translation initiation sequence was removed in order to secure control of the switch. The mCherry gene, excluding an 8-amino-acid sequence at the N-terminal thereof, was amplified using the pET28a-mCherry plasmid as a template and the BsaI-Trc-mcherry-F/SpeI-mCherry-R primer set shown in Table 2, and was then inserted into the pACYC* vector using BsaI and SpeI (BsaI and NheI restriction enzymes were used for vectors), and the sequence from the T7 promoter to the T7 terminator was cloned into the pCDF Duet vector using the EcoNI and Bsu36I restriction enzyme sequences to construct a genetic circuit for conducting transcription of mRNA that allows control of the switch but has no trigger (FIG. 4).

Next, BL21 (DE3) was transformed with txtl-Cis-sfGFP and pCDF-txtl-Trans-mCherry plasmids, and then GFP and mCherry fluorescence of cells were measured.

Figure 5:
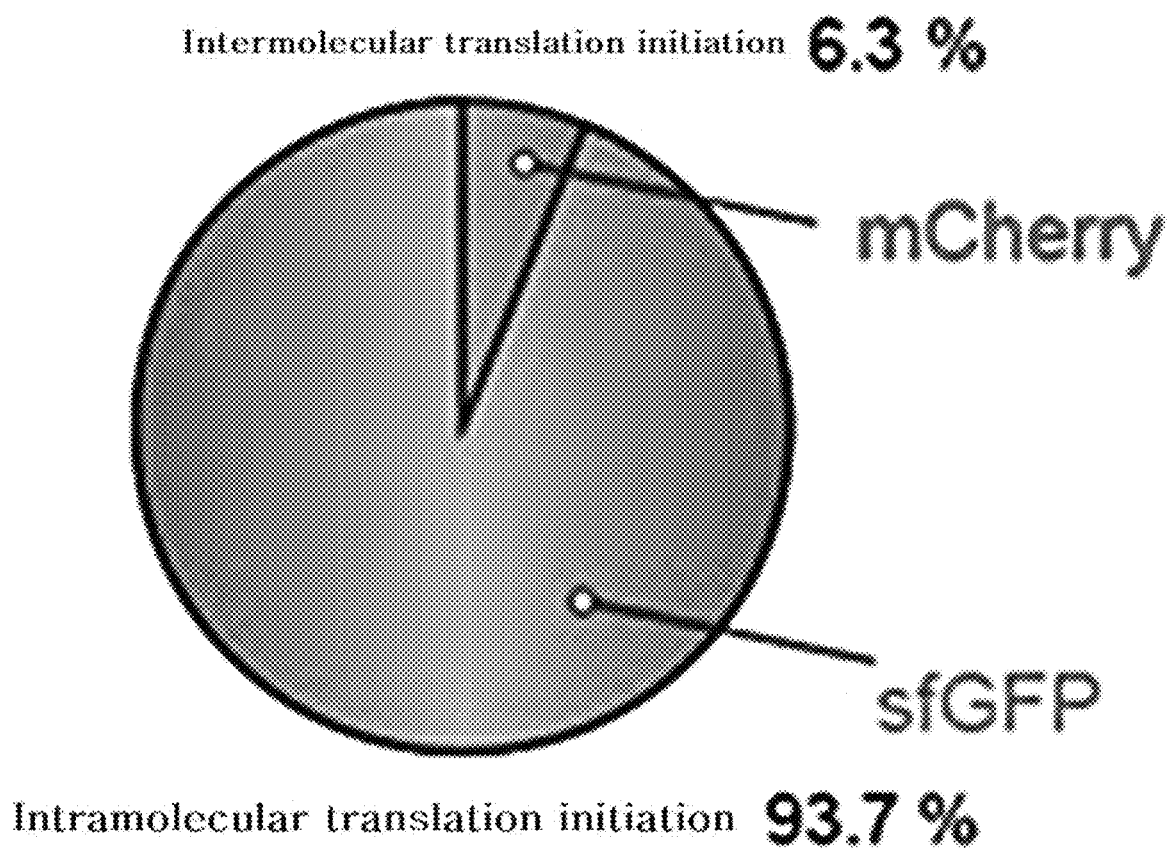
FIG. 5 is a graph showing the proportion of unit fluorescence of ProIntra cells using sfGFP protein as a marker (index) for initiation of translation by interaction in mRNA molecules.

As a result, as can be seen from FIG. 5, the ratio at which the 3'-end trigger sequence of txtl-Cis-sfGFP causes initiation of translation from the switch of pCDF-txtl-Trans-mCherry by the interaction between mRNA molecules is 6.3%, and the ratio at which the 3'-end trigger sequence of txtl-Cis-sfGFP causes initiation of translation from the switch of pCDF-txtl-Trans-mCherry by the interaction in mRNA molecules is 93.7%. That is, even if the same switch is present on different mRNA strands, the efficiency of translation initiation by the interaction in molecules having a trigger in the same mRNA strand is high.

Experimental Example 3: Comparison of Quality of Protein Produced from ProQC Gene Expression Cassette A long mRNA encoding a long protein is easily damaged during transcription. For this reason, whether or not the productivity of the long protein was improved when the ProQC gene expression cassette prepared in Example 1 was used was determined.

In order to produce a 4581-bp-long mCherry-lacZ-sfGFP (MLG) fusion protein as a model system, first, an amplification product BL21 (DE3), in which the stop codon of mCherry was removed and a linker was attached thereto, was prepared using the BsaI-Trc-mcherry-F/KpnI-Lnk-MR/Lnk-M-R primer set shown in Table 2 and using the pET28a plasmid as a template, a lacz gene amplification product, in which the start codon and the stop codon were removed, was prepared using a KpnI-lacZ-F/BsaI-lacz-R primer set and using chromosome as a template, and an sfGFP gene amplification product, in which a linker was attached to the amino terminal, was prepared using a BsaI-Lnk-sfGFP-F/SpeI-sfGFP-R primer set and the pBR322-J23100-sfGFP plasmid as a template. Among the three amplification products, the mCherry was cut with BsaI and KpnI restriction enzymes, the lacz was cut with KpnI and BsaI restriction enzymes, and the sfGFP was cut with BsaI and SpeI restriction enzymes. Then, the products were purified and ligated in one tube, and finally amplified using a BsaI-Trc-mcherry-F/SpeI-sfGFP-R primer set to conduct amplification of the strand to which three genes were connected in sequence, and then TA cloning was performed thereon.

Figure 6:
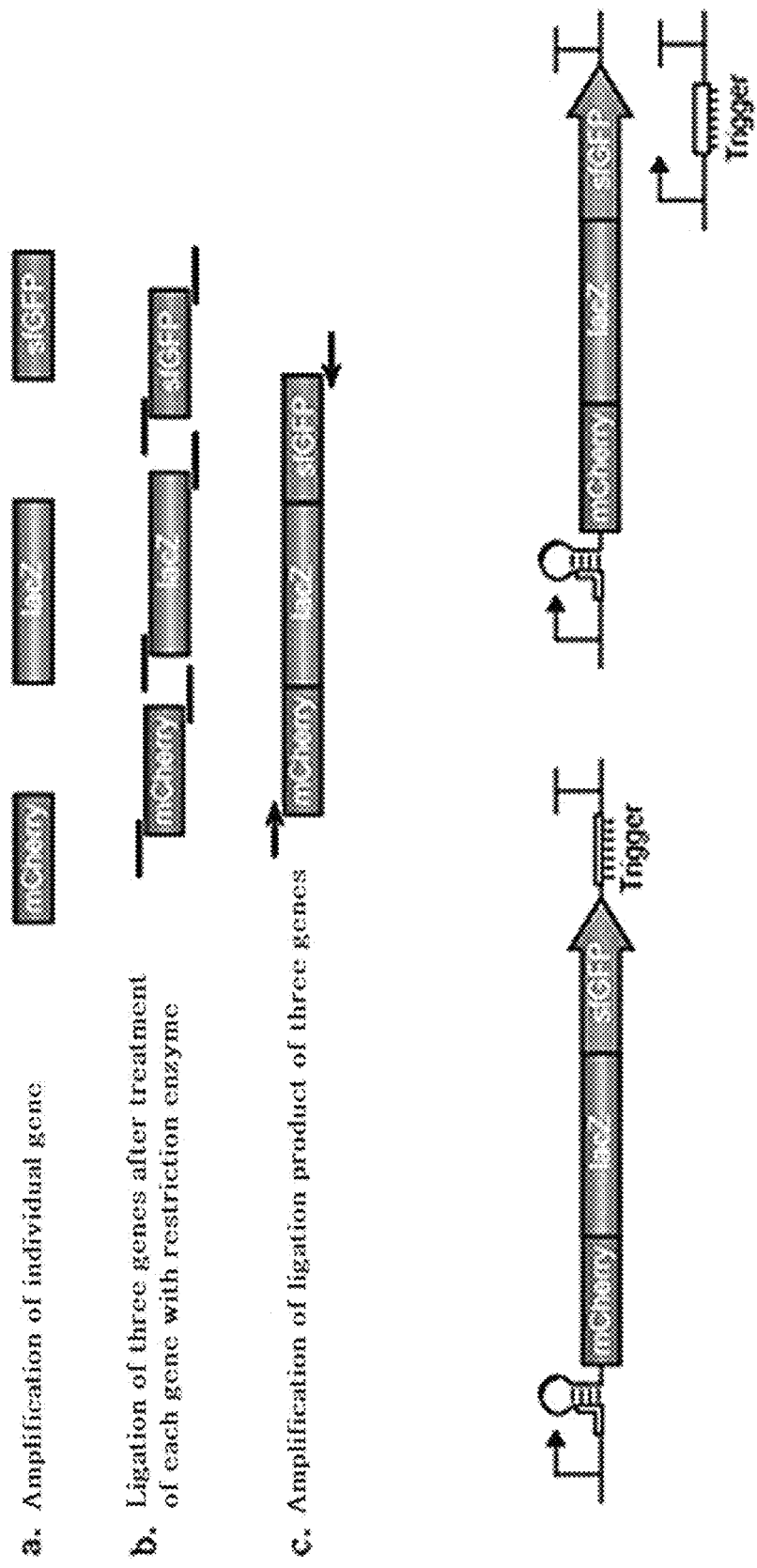
FIG. 6 is a schematic diagram illustrating a method for constructing an mCherry_lacZ_gfp (MLG) fusion protein, a ProQC-MLG plasmid-expressing MLG protein, and a ProNC-MLG gene.

The MLG was amplified using a BsaI-his-MF/SpeI-SacI-sfGFP-R primer set and a pMD19-MLG plasmid as a template, the vector sequence was amplified using a BsaI-Swit #3-R/SpeI-Trig-F primer set and a txtl-Cis-sfGFP plasmid as a template, and the resulting amplification products were cloned using BsaI and SpeI restriction enzyme sequences to construct a txtl-Cis-MLG_NH plasmid, and were cloned using BsaI and NheI restriction enzyme sequences to construct a txtl-Trans-MLG_NH plasmid (FIG. 6).

The mCherry-lacZ-sfGFP (MLG) fusion protein produced through the above process has an mCherry fluorescent protein at the amino terminal (5'-end) and an sfGFP fluorescent protein at the carboxyl terminal (3' end). Thus, whether or not the two ends of the long protein produced in cells are lost can be determined by measuring the ratio of mCherry and sfGFP fluorescence of individual cells.

Next, the unit fluorescence was calculated to convert the two types of fluorescence emitted from the cell into the number of molecules. For this purpose, the sfGFP gene was amplified using a Duet-F/His-G-R primer set shown in Table 2 and a txtl-Trans-sfGFP plasmid as a template, and six repeated histidine tags (6×His) were attached to the carboxyl terminal of sfGFP and then cloning into the pACYC* vector was conducted using EcoNI and SacI restriction enzyme sequences to construct a txtl-Trans-sfGFP CH plasmid. The mCherry gene was amplified using a Duet-F/His-MR primer set shown in Table 2 and a pCDF-txtl-Trans-mCherry plasmid as a template, and histidine tags (6×His) were attached to the carboxyl terminal of mCherry and then cloning into the pACYC* vector was conducted using EcoNI and SacI restriction enzymes to construct a txtl-Trans-mCherry_CH plasmid.

In addition, in order to calculate the fluorescence per unit mass of the fluorescent protein, a pair of the txtl-Trans-mCherry-CH plasmid and pCDF-Trigger plasmid was transformed into BL21 (DE3) to produce Unit-sfGFP, and a pair of the txtl-Trans-sfGFP plasmid and pCDF-Trigger plasmid was transformed into BL21 (DE3) to produce Unit-mCherry. Fluorescent proteins were expressed in the Unit-sfGFP and Unit-mCherry in the same manner as in Experimental Example 1. After 4 hours, the cells were harvested. The sfGFP and mCherry were each purified from the harvested cells by Ni-NTA purification, a protein purification method using histidine tags, and then the correlation between the protein amount and fluorescence intensity was determined. Here, the amount of the protein was measured by a Bradford assay, and the fluorescence was measured from the purified sample diluted with PBS buffer at various ratios. A formula describing the relationship between the protein amount and fluorescence intensity of each of sfGFP and mCherry was established (when measured with Hidex, a formula for fluorescence intensity per gram of protein was established).

Next, in order to prevent the lacz contained in BL21 (DE3) from being purified or bound with the MLG fusion protein, the lacZ gene was removed from the chromosome. In this case, gene removal was performed using a conventional gene recombination method using homology.

For this purpose, FRT-Kan-FRT was amplified using the lacZ-Del-F1/lacZ-Del-R1/lacz-Del-F2/lacz-Del-R2 primer set shown in Table 2 and the pFRT72 plasmid as a template, and was then treated with DpnI restriction enzyme to remove the template plasmid. The amplification product was subjected to PCR purification and ethanol concentration to transform the BL21 (DE3)/pKD46 strain expressing the recombinant enzyme. Additionally, the insertion of the FRT-Kan-FRT sequence, instead of the lacz gene, was identified through colony PCR using the lacz-check-F/lacZ-check-R primer set. Then, transformation with pCP20 plasmid and expression of the FLP recombinase were conducted to remove the kanamycin resistance gene ($Kan^R$) to thereby produce a BL21 (DE3) ΔlacZ strain.

The BL21 (DE3) ΔlacZ was transformed with a txtl-Cis-MLG/pCDF-Term plasmid pair to produce a ProQC-MLG strain, and was transformed with a txtl-Trans-MLG/pCDF-Trigger plasmid pair to produce a ProNC-MLG strain.

The ProQC-MLG and ProNC-MLG strains were incubated overnight in a LB (Lysogeny broth) medium containing Spec and Cam antibiotics, diluted to $OD_{600}$ of 0.05, followed by induction with 0.2 mM IPTG when $OD_{600}$ reached 0.8, to express a recombination protein. After 4 hours, the sfGFP and mCherry fluorescence of the cells was measured, divided by a unit fluorescence, and converted into the amounts of amino and carboxyl terminal of the MLG fusion protein in the cells, and then the values were normalized to the amounts of mCherry in respective systems. As can be seen from a) of FIG. 7, the proportion of the full-length protein including the carboxyl terminal (sfGFP) in the ProQC gene expression cassette was much higher than that of the natural gene expression cassette.

In addition, in order to determine the productivity of the fusion protein of the unit cells in ProQC-MLG and ProNC-MLG, the expression level of the full-length protein including the carboxyl terminal (sfGFP) was detected. As shown in b) of FIG. 7, the result shows that, when the expression level of ProNC-MLG was normalized to 1, the amount of full-length MLG fusion protein in each cell, when the ProQC gene expression cassette was applied, was also 1.7 times higher than that of ProNC-MLG.

Next, in order to determine the length distribution of the MLG fusion protein produced in the actual cell, the MLG fusion protein expressed from each of the ProQC-MLG and ProNC-MLG strains was purified using the 6× histidine tag at the amino terminal through a Ni-NTA method. When the amino-terminal tag is used, peptides synthesized from the corresponding expression cassette can be recovered without distinction therebetween. At this time, peptides that are terminated prematurely or that have not been translated to the stop codon due to mRNA degradation are also purified. As a control group for comparison with the experimental group, the txtl-Cis-MLF CH plasmid was transformed into BL21 (DE3) Δlacz, and then the MLG fusion protein, which had been completely translated to the end, was purified using a histidine tag at the carboxyl terminal, which was marked as "Full length".

For distinction on the SDS-PAGE gel, the concentration of the protein purified from ProQC and ProNC was measured through a Bradford assay, and the same amount of the protein was injected into one cell. As can be seen from FIG. 8, the result of SDS-PAGE showed that the protein purified from ProQC had a higher amount of full-length proteins and a lower amount of shortened proteins than the protein purified from ProNC, which was clearly distinguished from Full-length.

Meanwhile, the sequences, strains, plasmids and primer sequences used in Examples and Experimental Examples are shown in Tables 1 to 3 below.

TABLE 1

| Used strains and plasmids | | |
|---|---|---|
| | Related characteristics | Source |
| Strain name | | |
| Mach-T1$^R$ | E. coliF- 80(lacZ)ΔM15 ΔlacX74 hsdR(rK-mK+)ΔrecA1398 endA1 tonA | Invitrogen |
| BL21(DE3) | E. colistr. B F- ompT gal dcm lon hsdSB(rB-mB-) λ(DE3 [lacI lacUV5-T7p07 ind1 sam7 nin5])[malB+]K-12(λS) | Prior research |
| BL21(DE3)ΔlacZ | BL21(DE3)ΔlacZ | Present invention |

TABLE 1-continued

Used strains and plasmids

| | Related characteristics | Source |
|---|---|---|
| BL21(DE3)-NC | BL21(DE3)/pACYC_Duet/pCDF-Term | Present invention |
| ProQC-sfGFP | BL21(DE3)/txtl-Cis-sfGFP/pCDF-Term | Present invention |
| ProNC-sfGFP | BL21(DE3)/txtl-Trans-sfGFP/pCDF-Trigger | Present invention |
| ProIntra | BL21(DE3)/txtl-Cis-sfGFP/pCDF-txtl-Trans-mCherry | Present invention |
| Unit-sfGFP | BL21(DE3)/txtl-Trans-sfGFP_NH/pCDF-Trigger | Present invention |
| Unit-mCherry | BL21(DE3)/txtl-Trans-mCherry_NH/pCDF-Trigger | Present invention |
| BL21(DE3)ΔlacZ-NC | BL21(DE3)ΔlacZ/pACYC_Duet/pCDF-Term | Present invention |
| ProQC-MLG | BL21(DE3)ΔlacZ/txtl-Cis-MLG_NH/pCDF-Term | Present invention |
| ProNC-MLG | BL21(DE3)ΔlacZ/txtl-Trans-MLG_NH/pCDF-Trigger | Present invention |
| Plasmid name | | |
| pACYC_Duet | Expression vector, $Cm^R$, $p15A_{ori}$ | Novagen |
| pACYC* | pACYC_DuetΔNheI/$P_{T7}$-BsaI-NheI-$T_{T7}$ | Present invention |
| pCDF_Duet | Expression vector, $Sm^R$, $cloDF13_{ori}$ | Novagen |
| pBR322-J23100-sfGFP | pBR322/BBaJ23100-UTR-sfGFP | Prior research |
| pET28a-mCherry | pET28a-BBaJ23100-UTR-mCherry | Prior research |
| pMD19 | TA cloning vector | TaKaRa |
| txtl-Cis-sfGFP | pACYC*/$P_{T7}$-Switch#3-sfGFP-Trigger-$T_{T7}$ | Present invention |
| txtl-Trans-sfGFP | pACYC*/$P_{T7}$-Switch#3-sfGFP-$T_{T7}$ | Present invention |
| pCDF-Term | pCDF_Duet/$P_{T7}$-BsaI-NheI-$T_{T7}$ | Present invention |
| pCDF-Trigger | pCDF_Duet/$P_{T7}$-Trigger-$T_{T7}$ | Present invention |
| pCDF-txtl-Trans-mCherry | pCDF_Duet/$P_{T7}$-Switch#3-mCherry$^{Trc}$-$T_{T7}$ | Present invention |
| txtl-Trans-sfGFP_CH | pACYC*/$P_{T7}$-Switch#3-sfGFP_6XHis-$T_{T7}$ | Present invention |
| txtl-Trans-mCherry_CH | pACYC*/$P_{T7}$-Switch#3-mCherry$^{Trc}$_6XHis-$T_{T7}$ | Present invention |
| pMD19-MLG | pMD19/$P_{T7}$-Switch#3-mCherry$^{Trc}$_lacZ_sfGFP-Trigger-$T_{T7}$ | Present invention |
| txtl-Cis-MLG_NH | pACYC*/$P_{T7}$-Switch#3-6XHis_mCherry$^{Trc}$_lacZ_sfGFP-Trigger-$T_{T7}$ | Present invention |
| txtl-Trans-MLG_NH | pACYC*/$P_{T7}$-Switch#3-6XHis_MLG-$T_{T7}$ | Present invention |
| txtl-Cis-MLG_CH | pACYC*/$P_{T7}$-Switch#3-MLG_6XHis-Trigger-$T_{T7}$ | Present invention |
| txtl-Trans-MLG_CH | pACYC*/$P_{T7}$-Switch#3-MLG_6XHis-$T_{T7}$ | Present invention |
| pKD46 | Red recombinase expression vector, $Amp^R$ | Prior research |
| pFRT72 | pGEM-FRT-Kan-FRT variant | Prior research |
| pCP20 | FLP recombinase expression vecotor, $Amp^R$, $Cm^R$ | Prior research |

TABLE 2

Primer sequence used

| Primer name | Sequence |
|---|---|
| EcoNI-PT7-NheI-TT7-F | ACTCCTGCATTAGGAAATTAATACGACTCACTATAggagaccCG CAGCGcTAGCATAACCCCTTGGGGC (SEQ ID NO: 8) |
| SpeI-pACYC-R | ACCACTAGTGCTGATGTCCGGCG (SEQ ID NO: 9) |

TABLE 2-continued

Primer sequence used

| Primer name | Sequence |
| --- | --- |
| BsaI-Swit-sfGFP-F2 | cccGGTCTCCTATAGGGATCTATTACTACTTACCATTGTCTTGC TCTATacagaaacagaggagatATAGAatgAGACAATGGAACCTGGCG GCAGCGCAAAAG (SEQ ID NO: 10) |
| Swit-sfGFP-F1 | AGGAGATATAGAATGAGACAATGGAACCTGGCGGCAGCGCA AAAGGCTAGCAAGGGCGAGGAGC (SEQ ID NO: 11) |
| SpeI-SacI-sfGFP-R | GGGACATCGGAATGTCCCATCAGACTAGTCAATACGATTACT TTCTGTGAGCTCACTTGTACAGCTCGTCCATGC (SEQ ID NO: 12) |
| BsaI-Titg-R2 | TATggtctctCTAgCTTATCTATTACTACTTACCATTGTCTTGCTCT TATTGATGGGACATCGGAATGTCCCATC (SEQ ID NO: 13) |
| BsaI-Trigger#3-F | cccGGTCTCCTATAGGGTGATGGGACATTCCGATGTCC (SEQ ID NO: 14) |
| BsaI-Trc-mcherry-F | ACAGGTCTCTCTAGCGCTATCATTAAAGAGTTCATGCG (SEQ ID NO: 15) |
| SpeI-mCherry-R | CAGACTAGTCAATACGATTACTTTCTGTGAGCTCATTTGTACA GCTCATCCATGC (SEQ ID NO: 16) |
| Duet-F | CGGGATCTCGACGCTCTCC (SEQ ID NO: 17) |
| His-G-R | TGTACTAGTGAGCTCATTAGTGATGGTGATGGTGATGCTTGT ACAGCTCGTCCATGCCGAG (SEQ ID NO: 18) |
| His-M-R | TGTACTAGTGAGCTCATTAGTGATGGTGATGGTGATGTTTGT ACAGCTCATCCATG (SEQ ID NO: 19) |
| lacZ-Del-F1 | GCCGTTCGACGATTCTCCATATGGGAGTACTCGCGGTTGACT GAG (SEQ ID NO: 20) |
| lacZ-Del-R1 | CTAGCAAGAATCATATGGAGAGCGAGTGCTGGAGCGAACTG CGAAG (SEQ ID NO: 21) |
| lacZ-Del-F2 | GCAGACATGGCCTGCCCGGTTATTATTATTTTTGACACCAGA GCCGTTCGACGATTCTCCATATG (SEQ ID NO: 22) |
| lacZ-Del-R2 | GGCTCGTATGTTGTGTGGAAATTGTGAGCGGATAACAATTTCA CACACTAGCAAGAATCATATGGAGAGCG (SEQ ID NO: 23) |
| lacZ-check-F | TCACTTTTGCTGATATGGTTGATGTC (SEQ ID NO: 24) |
| lacZ-check-R | CGACTGGAAAGCGGGCAGTGAG (SEQ ID NO: 25) |
| KpnI-Lnk-M-R | ACGGTCTCCATGGTACCAGCACTACCAGCAC (SEQ ID NO: 26) |
| Lnk-M-R | CTTGCTAGCACCAGCACTACCAGCACTACCAGCACTATCTTT GTACAGCTCATCCATG (SEQ ID NO: 27) |
| KpnI-lacZ-F | AGTGGTCTCACCATGATTACGGATTCACTG (SEQ ID NO: 28) |
| BsaI-lacZ-R | ACCGGTCTCTGAATCTTTTTGACACCAGACCAAC (SEQ ID NO: 29) |
| BsaI-Lnk-sfGFP-F | AGCGGTCTCGATTCAGCAGGCTCAGCAGGCTCAGCAGGCGCT AGCAAGGGCGAGG (SEQ ID NO: 30) |
| SpeI-sfGFP-R | CAGACTAGTCAATACGATTACTTTCTGTGAGCTC (SEQ ID NO: 31) |
| BsaI-Swit#3-R | ATTGGTCTCTCTAGCCTTTTGCGCTGCCGCCAGG (SEQ ID NO: 32) |
| SpeI-Trig-F | TGACTAGTCTGATGGGACATTCCGATGTCCCATCAATAAGAG CAAGACAATGGTAAGTAG (SEQ ID NO: 33) |
| BsaI-his-M-F | AAGGGTCTCACTAGCCATCACCATCACCATCACGCTATCATT AAAGAGTTCATGCG (SEQ ID NO: 34) |

TABLE 3

Toehold switch and gene sequences

| Toehold switch | Remarks |
| --- | --- |
| switch#3 (DNA Sequence) | SEQ ID NO: 1 |
| switch#3 (DNA Sequence) | SEQ ID NO: 2 |
| Trigger#3 (DNA Sequence) | SEQ ID NO: 3 |
| Trigger#3 (DNA Sequence) | SEQ ID NO: 4 |

TABLE 3-continued

Toehold switch and gene sequences

| Gene | Remarks |
| --- | --- |
| mCherry$^{Trc}$ | SEQ ID NO: 5 |
| sfGFP | SEQ ID NO: 6 |
| mcherry_lacZ_sfGFP | SEQ ID NO: 7 |

The invention claimed is:

1. A DNA molecule capable of forming a stem loop structure during transcription into mRNA, the stem loop structure having a ribosome-binding site located therein, the DNA molecule comprising:
   a first DNA sequence encoding a first RNA sequence designed such that a part of the first RNA sequence can participate in a formation of the stem loop structure; and
   a second DNA sequence encoding a second RNA sequence located after a stop codon that can complementarily bind to the first RNA sequence designed such that the part of the first RNA sequence can participate in the formation of the stem loop structure.

2. The DNA molecule according to claim 1, wherein the DNA molecule comprises a multiple cloning site after the ribosome-binding site and before the second DNA sequence.

3. A vector comprising the DNA molecule according to claim 1.

4. An mRNA forming a stem loop structure, the stem loop structure having a ribosome-binding site located therein, the mRNA comprising:
   a first RNA sequence having a part of the sequence participating in the stem loop structure; and
   a second RNA sequence having a complementary sequence capable of binding to the first RNA sequence and being located after a stop codon.

5. The mRNA according to claim 4, wherein the mRNA initiates translation while the stem loop structure is released when the second RNA sequence binds to the first RNA sequence.

6. The mRNA according to claim 5, wherein the translation is initiated when a ribosome binds to the ribosome-binding site.

* * * * *

```
                       SEQUENCE LISTING

<160> NUMBER OF SEQ ID NOS: 34

<210> SEQ ID NO 1
<211> LENGTH: 90
<212> TYPE: DNA
<213> ORGANISM: Artificial Sequence
<220> FEATURE:
<223> OTHER INFORMATION: switch#3 DNA

<400> SEQUENCE: 1
gggatctatt actacttacc attgtcttgc tctatacaga aacagaggag atatagaatg    60
agacaatgga acctggcggc agcgcaaaag                                     90

<210> SEQ ID NO 2
<211> LENGTH: 90
<212> TYPE: RNA
<213> ORGANISM: Artificial Sequence
<220> FEATURE:
<223> OTHER INFORMATION: switch#3 RNA

<400> SEQUENCE: 2
gggaucuauu acuacuuacc auugucuugc ucuauacaga aacagaggag auauagaaug    60
agacaaugga accuggcggc agcgcaaaag                                     90

<210> SEQ ID NO 3
<211> LENGTH: 62
<212> TYPE: DNA
<213> ORGANISM: Artificial Sequence
<220> FEATURE:
<223> OTHER INFORMATION: trigger#3 DNA

<400> SEQUENCE: 3
tgatgggaca ttccgatgtc ccatcaataa gagcaagaca atggtaagta gtaatagata    60
ag                                                                   62

<210> SEQ ID NO 4
<211> LENGTH: 62
<212> TYPE: RNA
<213> ORGANISM: Artificial Sequence
<220> FEATURE:
<223> OTHER INFORMATION: trigger#3 RNA

<400> SEQUENCE: 4
ugaugggaca uuccgauguc ccaucaauaa gagcaagaca augguaagua guaauagaua    60
ag                                                                   62

<210> SEQ ID NO 5
<211> LENGTH: 690
<212> TYPE: DNA
<213> ORGANISM: Artificial Sequence
<220> FEATURE:
```

<223> OTHER INFORMATION: mCherry Trc

<400> SEQUENCE: 5

| | | |
|---|---|---|
| atggctagcg ctatcattaa agagttcatg cgcttcaaag ttcacatgga gggttctgtt | 60 |
| aacggtcacg agttcgagat cgaaggcgaa ggtgagggcc gtccgtatga aggcacccag | 120 |
| accgccaaac tgaaagtgac taaaggcggc ccgctgcctt ttgcgtggga catcctgagc | 180 |
| ccgcaattta tgtacggttc taaagcttat gttaaacacc cagcggatat cccggactat | 240 |
| ctgaagctgt cttttccgga aggtttcaag tgggaacgcg taatgaattt tgaagatggt | 300 |
| ggtgtcgtga ccgtcactca ggactcctcc ctgcaggatg cgagttcat ctataaagtt | 360 |
| aaactgcgtg gtactaattt tccatctgat ggcccggtga tgcagaagaa gacgatgggt | 420 |
| tgggaggcgt ctagcgaacg catgtacccg aagatggtg cgctgaaagg cgaaattaaa | 480 |
| cagcgcctga aactgaaaga tggcggccat tatgacgctg aagtgaaaac cacgtacaaa | 540 |
| gccaagaaac ctgtgcagct gcctggcgcg tacaatgtga atattaaact ggacatcacc | 600 |
| tctcataatg aagattatac gatcgtagag caatatgagc gcgcggaggg tcgtcattct | 660 |
| accggtggca tggatgagct gtacaaatga | 690 |

<210> SEQ ID NO 6
<211> LENGTH: 720
<212> TYPE: DNA
<213> ORGANISM: Aequorea victoria

<400> SEQUENCE: 6

| | | |
|---|---|---|
| atggctagca agggcgagga gctgttcacc ggggtggtgc ccatcctggt cgagctggac | 60 |
| ggcgacgtaa acggccacaa gttcagcgtg cgcggcgagg gcgagggcga tgccaccaac | 120 |
| ggcaagctga ccctgaagtt catctgcacc accggcaagc tgcccgtgcc ctggcccacc | 180 |
| ctcgtgacca cccctgaccta cggcgtgcag tgcttcagcc gctaccccga ccacatgaag | 240 |
| cagcacgact tcttcaagtc cgccatgccc gaaggctacg tccaggagcg caccatcagc | 300 |
| ttcaaggacg acggcaccta caagacccgc gccgaggtga agttcgaggg cgacaccctg | 360 |
| gtgaaccgca tcgagctgaa gggcatcgac ttcaaggagg acggcaacat cctggggcac | 420 |
| aagctggagt acaacttcaa cagccacaac gtctatatca ccgccgacaa gcagaagaac | 480 |
| ggcatcaagg ccaacttcaa gatccgccac aacgtggagg acggcagcgt gcagctcgcc | 540 |
| gaccactacc agcagaacac ccccatcggc gacggccccg tgctgctgcc cgacaaccac | 600 |
| tacctgagca cccagtccgt gctgagcaaa gaccccaacg agaagcgcga tcacatggtc | 660 |
| ctgctggagt tcgtgaccgc cgccgggatc actctcggca tggacgagct gtacaagtga | 720 |

<210> SEQ ID NO 7
<211> LENGTH: 4527
<212> TYPE: DNA
<213> ORGANISM: Escherichia coli

<400> SEQUENCE: 7

| | | |
|---|---|---|
| atggctatca ttaaagagtt catgcgcttc aaagttcaca tggagggttc tgttaacggt | 60 |
| cacgagttcg agatcgaagg cgaaggtgag ggccgtccgt atgaaggcac ccagaccgcc | 120 |
| aaactgaaag tgactaaagg cggcccgctg ccttttgcgt gggacatcct gagcccgcaa | 180 |
| tttatgtacg gttctaaagc ttatgttaaa cacccagcgg atatcccgga ctatctgaag | 240 |
| ctgtcttttc cggaaggttt caagtgggaa cgcgtaatga attttgaaga tggtggtgtc | 300 |
| gtgaccgtca ctcaggactc ctccctgcag gatgcgagt tcatctataa agttaaactg | 360 |

```
cgtggtacta attttccatc tgatggcccg gtgatgcaga agaagacgat gggttgggag      420
gcgtctagcg aacgcatgta cccggaagat ggtgcgctga aaggcgaaat taaacagcgc      480
ctgaaactga agatggcgg ccattatgac gctgaagtga aaccacgta caaagccaag       540 aaacctgtgc agctgcctgg cgcgtacaat gtgaatatta actgacat cacctctcat        600 aatgaagatt atacgatcgt agagcaatat gagcgcgcgg agggtcgtca ttctaccggt      660
ggcatggatg agctgtacaa agatagtgct ggtagtgctg gtagtgctgg taccatgatt      720
tcggattcac tggccgtcgt tttacaacgt cgtgactggg aaaaccctgg cgttacccaa      780
cttaatcgcc ttgcagcaca tccccctttc gccagctggc gtaatagcga agaggcccgc      840
accgatcgcc cttcccaaca gttgcgcagc ctgaatggcg aatggcgctt tgcctggttt      900
ccggcaccag aagcggtgcc ggaaagctgg ctggagtgcg atcttcctga ggccgatact      960
gtcgtcgtcc cctcaaactg gcagatgcac ggttacgatg cgcccatcta caccaacgtg     1020
acctatccca ttacggtcaa tccgccgttt gttcccacgg agaatccgac gggttgttac     1080
tcgctcacat ttaatgttga tgaaagctgg ctacaggaag gccagacgcg aattattttt     1140
gatggcgtta actcggcgtt tcatctgtgg tgcaacgggc gctgggtcgg ttacggccag     1200
gacagtcgtt tgccgtctga atttgacctg agcgcatttt tacgcgccgg agaaaaccgc     1260
ctcgcggtga tggtgctgcg ctggagtgac ggcagttatc tggaagatca ggatatgtgg     1320
cggatgagcg gcattttccg tgacgtctcg ttgctgcata aaccgactac acaaatcagc     1380
gatttccatg ttgccactcg ctttaatgat gatttcagcc gcgctgtact ggaggctgaa     1440
gttcagatgt gcggcgagtt gcgtgactac ctacgggtaa cagtttcttt atggcagggt     1500
gaaacgcagg tcgccagcgg caccgcgcct ttcggcggtg aaattatcga tgagcgtggt     1560
ggttatgccg atcgcgtcac actacgtctg aacgtcgaaa acccgaaact gtggagcgcc     1620
gaaatcccga atctctatcg tgcggtggtt gaactgcaca ccgccgacgg cacgctgatt     1680
gaagcagaag cctgcgatgt cggttttcgc gaggtgcgga ttgaaaatgg tctgctgctg     1740
ctgaacggca agccgttgct gattcgaggc gttaaccgtc acgagcatca tcctctgcat     1800
ggtcaggtca tggatgagca gacgatggtg caggatatcc tgctgatgaa gcagaacaac     1860
tttaacgccg tgcgctgttc gcattatccg aaccatccgc tgtggtacac gctgtgcgac     1920
cgctacggcc tgtatgtggt ggatgaagcc aatattgaaa cccacggcat ggtgccaatg     1980
aatcgtctga ccgatgatcc gcgctggcta ccggcgatga gcgaacgcgt aacgcgaatg     2040
gtgcagcgcg atcgtaatca cccgagtgtg atcatctggt cgctggggaa tgaatcaggc     2100
cacggcgcta atcacgacgc gctgtatcgc tggatcaaat ctgtcgatcc ttcccgcccg     2160
gtgcagtatg aaggcggcgg agccgacacc acggccaccg atattatttg cccgatgtac     2220
gcgcgcgtgg atgaagacca gcccttcccg gctgtgccga atggtccat caaaaaatgg    2280 ctttcgctac ctggagagac gcgcccgctg atcctttgcg aatacgccca cgcgatgggt     2340
aacagtcttg gcggtttcgc taaatactgg caggcgtttc gtcagtatcc ccgtttacag     2400
ggcggcttcg tctgggactg ggtggatcag tcgctgatta aatatgatga aaacggcaac     2460
ccgtggtcgc cttacggcgg tgattttggc gatacgccca acgatcgcca gttctgtatg     2520
aacggtctgg tctttgccga ccgcacgccg catccagcgc tgacggaagc aaaacaccag     2580 cagcagttt tccagttccg tttatccggg caaaccatcg aagtgaccag cgaataccctg     2640 ttccgtcata gcgataacga gctcctgcac tggatggtgg cgctggatgg taagccgctg     2700
```

```
gcaagcggtg aagtgcctct ggatgtcgct ccacaaggta acagttgat tgaactgcct      2760 gaactaccgc agccggagag cgccgggcaa ctctggctca cagtacgcgt agtgcaaccg      2820
aacgcgaccg catggtcaga agccgggcac atcagcgcct ggcagcagtg gcgtctggcg      2880
gaaaacctca gtgtgacgct ccccgccgcg tcccacgcca tcccgcatct gaccaccagc      2940
gaaatggatt tttgcatcga gctgggtaat aagcgttggc aatttaaccg ccagtcaggc      3000
tttctttcac agatgtggat tggcgataaa aaacaactgc tgacgccgct gcgcgatcag      3060
ttcacccgtg caccgctgga taacgacatt ggcgtaagtg aagcgacccg cattgaccct      3120
aacgcctggg tcgaacgctg gaaggcggcg ggccattacc aggccgaagc agcgttgttg      3180
cagtgcacgg cagatacact tgctgatgcg gtgctgatta cgaccgctca cgcgtggcag      3240
catcagggga aaaccttatt tatcagccgg aaaacctacc ggattgatgg tagtggtcaa      3300
atggcgatta ccgttgatgt tgaagtggcg agcgatacac cgcatccggc gcggattggc      3360
ctgaactgcc agctggcgca ggtagcagag cgggtaaact ggctcggatt agggccgcaa      3420
gaaaactatc ccgaccgcct tactgccgcc tgttttgacc gctgggatct gccattgtca      3480
gacatgtata ccccgtacgt cttcccgagc gaaaacggtc tgcgctgcgg gacgcgcgaa      3540
ttgaattatg cccacaccca gtggcgcggc gacttccagt tcaacatcag ccgctacagt      3600
caacagcaac tgatggaaac cagccatcgc catctgctgc acgcggaaga aggcacatgg      3660
ctgaatatcg acggtttcca tatggggatt ggtggcgacg actcctggag cccgtcagta      3720
tcggcggaat ccagctgag cgccggtcgc taccattacc agttggtctg gtgtcaaaaa      3780
gattcagcag gctcagcagg ctcagcaggc gctagcaagg gcgaggagct gttcaccggg      3840
gtggtgccca tcctggtcga gctggacggc gacgtaaacg gccacaagtt cagcgtgcgc      3900
ggcgagggcg agggcgatgc caccaacggc aagctgaccc tgaagttcat ctgcaccacc      3960
ggcaagctgc ccgtgccctg gcccaccctc gtgaccaccc tgacctacgg cgtgcagtgc      4020
ttcagccgct accccgacca catgaagcag cacgacttct tcaagtccgc catgcccgaa      4080
ggctacgtcc aggagcgcac catcagcttc aaggacgacg gcacctacaa gacccgcgcc      4140
gaggtgaagt tcgagggcga caccctggtg aaccgcatcg agctgaaggg catcgacttc      4200
aaggaggacg gcaacatcct ggggcacaag ctggagtaca acttcaacag ccacaacgtc      4260
tatatcaccg ccgacaagca gaagaacggc atcaaggcca acttcaagat ccgccacaac      4320
gtggaggacg gcagcgtgca gctcgccgac cactaccagc agaacacccc catcggcgac      4380
ggccccgtgc tgctgcccga caaccactac ctgagcaccc agtccgtgct gagcaaagac      4440
cccaacgaga gcgcgatca catggtcctg ctggagttcg tgaccgccgc cgggatcact      4500
ctcggcatgg acgagctgta caagtga                                        4527
```

<210> SEQ ID NO 8
<211> LENGTH: 69
<212> TYPE: DNA
<213> ORGANISM: Artificial Sequence
<220> FEATURE:
<223> OTHER INFORMATION: EcoNI-PT7-NheI-TT7-F

<400> SEQUENCE: 8

```
actcctgcat taggaaatta atacgactca ctataggaga cccgcagcgc tagcataacc      60
ccttggggc                                                              69
```

<210> SEQ ID NO 9
<211> LENGTH: 23

```
<212> TYPE: DNA
<213> ORGANISM: Artificial Sequence
<220> FEATURE:
<223> OTHER INFORMATION: SpeI-pACYC-R

<400> SEQUENCE: 9
accactagtg ctgatgtccg gcg                                          23

<210> SEQ ID NO 10
<211> LENGTH: 104
<212> TYPE: DNA
<213> ORGANISM: Artificial Sequence
<220> FEATURE:
<223> OTHER INFORMATION: BsaI-Swit-sfGFP-F2

<400> SEQUENCE: 10
cccggtctcc tatagggatc tattactact taccattgtc ttgctctata cagaaacaga   60
ggagatatag aatgagacaa tggaacctgg cggcagcgca aaag                  104

<210> SEQ ID NO 11
<211> LENGTH: 64
<212> TYPE: DNA
<213> ORGANISM: Artificial Sequence
<220> FEATURE:
<223> OTHER INFORMATION: Swit-sfGFP-F1

<400> SEQUENCE: 11
aggagatata gaatgagaca atggaacctg gcggcagcgc aaaaggctag caagggcgag   60
gagc                                                               64

<210> SEQ ID NO 12
<211> LENGTH: 75
<212> TYPE: DNA
<213> ORGANISM: Artificial Sequence
<220> FEATURE:
<223> OTHER INFORMATION: SpeI-SacI-sfGFP-R

<400> SEQUENCE: 12
gggacatcgg aatgtcccat cagactagtc aatacgatta ctttctgtga gctcacttgt   60
acagctcgtc catgc                                                   75

<210> SEQ ID NO 13
<211> LENGTH: 75
<212> TYPE: DNA
<213> ORGANISM: Artificial Sequence
<220> FEATURE:
<223> OTHER INFORMATION: BsaI-Trig-R2

<400> SEQUENCE: 13
tatggtctct ctagcttatc tattactact taccattgtc ttgctcttat tgatgggaca   60
tcggaatgtc ccatc                                                   75

<210> SEQ ID NO 14
<211> LENGTH: 38
<212> TYPE: DNA
<213> ORGANISM: Artificial Sequence
<220> FEATURE:
<223> OTHER INFORMATION: BsaI-Trigger#3-F

<400> SEQUENCE: 14
cccggtctcc tagggtga tgggacattc cgatgtcc                            38

<210> SEQ ID NO 15
```

```
<211> LENGTH: 38
<212> TYPE: DNA
<213> ORGANISM: Artificial Sequence
<220> FEATURE:
<223> OTHER INFORMATION: BsaI-Trc-mcherry-F

<400> SEQUENCE: 15
acaggtctct ctagcgctat cattaaagag ttcatgcg                             38

<210> SEQ ID NO 16
<211> LENGTH: 55
<212> TYPE: DNA
<213> ORGANISM: Artificial Sequence
<220> FEATURE:
<223> OTHER INFORMATION: SpeI-mCherry-R

<400> SEQUENCE: 16
cagactagtc aatacgatta ctttctgtga gctcatttgt acagctcatc catgc          55

<210> SEQ ID NO 17
<211> LENGTH: 19
<212> TYPE: DNA
<213> ORGANISM: Artificial Sequence
<220> FEATURE:
<223> OTHER INFORMATION: Duet-F

<400> SEQUENCE: 17
cgggatctcg acgctctcc                                                  19

<210> SEQ ID NO 18
<211> LENGTH: 61
<212> TYPE: DNA
<213> ORGANISM: Artificial Sequence
<220> FEATURE:
<223> OTHER INFORMATION: His-G-R

<400> SEQUENCE: 18
tgtactagtg agctcattag tgatggtgat ggtgatgctt gtacagctcg tccatgccga     60
g                                                                     61

<210> SEQ ID NO 19
<211> LENGTH: 56
<212> TYPE: DNA
<213> ORGANISM: Artificial Sequence
<220> FEATURE:
<223> OTHER INFORMATION: His-M-R

<400> SEQUENCE: 19
tgtactagtg agctcattag tgatggtgat ggtgatgttt gtacagctca tccatg         56

<210> SEQ ID NO 20
<211> LENGTH: 45
<212> TYPE: DNA
<213> ORGANISM: Artificial Sequence
<220> FEATURE:
<223> OTHER INFORMATION: lacZ-Del-F1

<400> SEQUENCE: 20
gccgttcgac gattctccat atgggagtac tcgcggttga ctgag                     45

<210> SEQ ID NO 21
<211> LENGTH: 46
<212> TYPE: DNA
<213> ORGANISM: Artificial Sequence
<220> FEATURE:
<223> OTHER INFORMATION: lacZ-Del-R1
```

<400> SEQUENCE: 21
ctagcaagaa tcatatggag agcgagtgct ggagcgaact gcgaag         46

<210> SEQ ID NO 22
<211> LENGTH: 65
<212> TYPE: DNA
<213> ORGANISM: Artificial Sequence
<220> FEATURE:
<223> OTHER INFORMATION: lacZ-Del-F2

<400> SEQUENCE: 22
gcagacatgg cctgcccggt tattattatt tttgacacca gagccgttcg acgattctcc    60
atatg    65

<210> SEQ ID NO 23
<211> LENGTH: 70
<212> TYPE: DNA
<213> ORGANISM: Artificial Sequence
<220> FEATURE:
<223> OTHER INFORMATION: lacZ-Del-R2

<400> SEQUENCE: 23
ggctcgtatg ttgtgtgaaa ttgtgagcgg ataacaattt cacacactag caagaatcat    60
atggagagcg    70

<210> SEQ ID NO 24
<211> LENGTH: 26
<212> TYPE: DNA
<213> ORGANISM: Artificial Sequence
<220> FEATURE:
<223> OTHER INFORMATION: lacZ-check-F

<400> SEQUENCE: 24
tcacttttgc tgatatggtt gatgtc         26

<210> SEQ ID NO 25
<211> LENGTH: 22
<212> TYPE: DNA
<213> ORGANISM: Artificial Sequence
<220> FEATURE:
<223> OTHER INFORMATION: lacZ-check-R

<400> SEQUENCE: 25
cgactggaaa gcgggcagtg ag         22

<210> SEQ ID NO 26
<211> LENGTH: 31
<212> TYPE: DNA
<213> ORGANISM: Artificial Sequence
<220> FEATURE:
<223> OTHER INFORMATION: KpnI-Lnk-M-R

<400> SEQUENCE: 26
acggtctcca tggtaccagc actaccagca c         31

<210> SEQ ID NO 27
<211> LENGTH: 58
<212> TYPE: DNA
<213> ORGANISM: Artificial Sequence
<220> FEATURE:
<223> OTHER INFORMATION: Lnk-M-R

<400> SEQUENCE: 27
cttgctagca ccagcactac cagcactacc agcactatct ttgtacagct catccatg    58

<210> SEQ ID NO 28
<211> LENGTH: 30
<212> TYPE: DNA
<213> ORGANISM: Artificial Sequence
<220> FEATURE:
<223> OTHER INFORMATION: KpnI-lacZ-F

<400> SEQUENCE: 28
agtggtctca ccatgattac ggattcactg    30

<210> SEQ ID NO 29
<211> LENGTH: 34
<212> TYPE: DNA
<213> ORGANISM: Artificial Sequence
<220> FEATURE:
<223> OTHER INFORMATION: BsaI-lacZ-R

<400> SEQUENCE: 29
accggtctct gaatcttttt gacaccagac caac    34

<210> SEQ ID NO 30
<211> LENGTH: 55
<212> TYPE: DNA
<213> ORGANISM: Artificial Sequence
<220> FEATURE:
<223> OTHER INFORMATION: BsaI-Lnk-sfGFP-F

<400> SEQUENCE: 30
agcggtctcg attcagcagg ctcagcaggc tcagcaggcg ctagcaaggg cgagg    55

<210> SEQ ID NO 31
<211> LENGTH: 34
<212> TYPE: DNA
<213> ORGANISM: Artificial Sequence
<220> FEATURE:
<223> OTHER INFORMATION: SpeI-sfGFP-R

<400> SEQUENCE: 31
cagactagtc aatacgatta ctttctgtga gctc    34

<210> SEQ ID NO 32
<211> LENGTH: 34
<212> TYPE: DNA
<213> ORGANISM: Artificial Sequence
<220> FEATURE:
<223> OTHER INFORMATION: BsaI-Swit#3-R

<400> SEQUENCE: 32
attggtctct ctagcctttt gcgctgccgc cagg    34

<210> SEQ ID NO 33
<211> LENGTH: 60
<212> TYPE: DNA
<213> ORGANISM: Artificial Sequence
<220> FEATURE:
<223> OTHER INFORMATION: SpeI-Trig-F

<400> SEQUENCE: 33
tgactagtct gatgggacat tccgatgtcc catcaataag agcaagacaa tggtaagtag    60

<210> SEQ ID NO 34
<211> LENGTH: 56
<212> TYPE: DNA
<213> ORGANISM: Artificial Sequence

```
<220> FEATURE:
<223> OTHER INFORMATION: BsaI-his-M-F

<400> SEQUENCE: 34
aagggtctca ctagccatca ccatcaccat cacgctatca ttaaagagtt catgcg       56
```